United States Patent [19]
Dulebohn

[11] Patent Number: 4,761,028
[45] Date of Patent: Aug. 2, 1988

[54] SINGLE-PIECE TWEEZERS

[75] Inventor: David H. Dulebohn, Tonka Bay, Minn.

[73] Assignee: Andrew Tool Company, Plymouth, Minn.

[21] Appl. No.: 49,110

[22] Filed: May 11, 1987

[51] Int. Cl.⁴ .................. A61B 17/30; A61B 17/32
[52] U.S. Cl. ................... 294/99.2; 128/354
[58] Field of Search ............ 294/99.2, 16; 128/354, 128/321, 346

[56] References Cited

U.S. PATENT DOCUMENTS

| | | | |
|---|---|---|---|
| 3,115,360 | 12/1963 | Witkoff | 294/99.2 |
| 3,653,389 | 4/1972 | Shannon | 294/99.2 |
| 4,020,846 | 5/1977 | Stokes | 294/99.2 |
| 4,452,106 | 6/1984 | Tartaglia | 294/99.2 |

Primary Examiner—James B. Marbert
Attorney, Agent, or Firm—Zarley, McKee, Thomte, Voorhees & Sease

[57] ABSTRACT

A means and method for forming tweezers and tweezers handles out of a single piece of material. The tweezers consist of unitary body including two parallel spaced apart arms which extend from an integrally formed heel end portion The ends of the arms opposite the heel end portion comprise tweezer tips or can be connected to replaceable tweezer tips. In a preferred embodiment, the single piece tweezers are produced by electrical discharge machine process which produces very accurate and precise cuts.

21 Claims, 1 Drawing Sheet

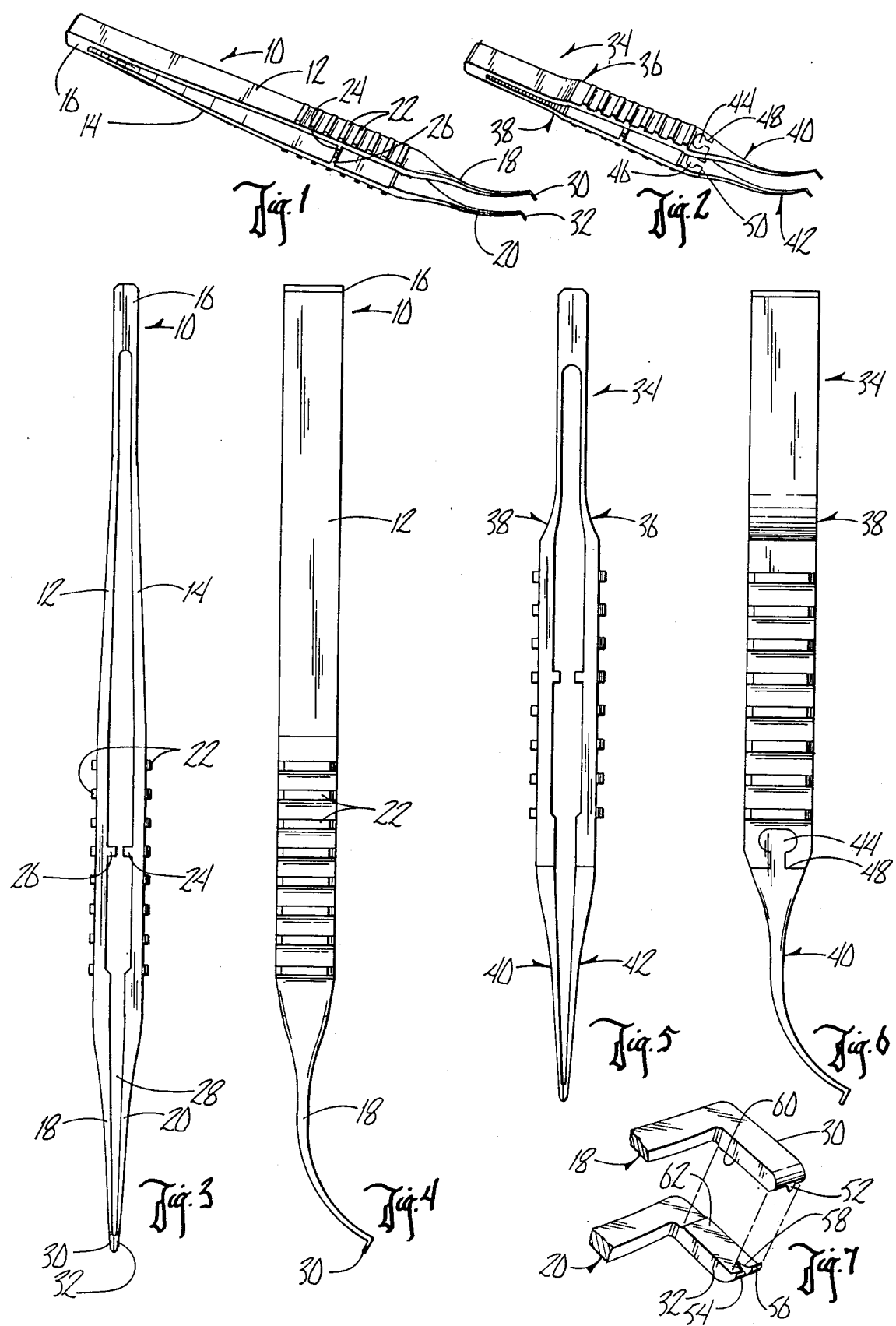

SINGLE-PIECE TWEEZERS

BACKGROUND OF THE INVENTION a. Field of the Invention

This invention relates to a tweezers, and in particular, a means and method for producing a single-piece tweezers and tweezers handles.

b. Problems in the Art

Conventional tweezers require tweezers or gripping tips which accurately and correspondingly come together upon convergence of the tweezers handles, and which also can securely hold even the smallest of objects. Such preciseness, accuracy and reliable gripping capacity is especially important in tweezers used for such purposes as surgery.

Manufacturing of accurate and reliable tweezers involves significant expense. Conventional tweezers have parallel elongated gripping arms which are separately manufactured and then joined at their rearward ends by fastening means, some type of joint, or by brazing. For precise instruments, welding of the two gripping arms is generally not possible because the high temperature would deform or otherwise jeopardize the accuracy and shape of the gripping means.

A particular and substantial problem with conventional metal tweezers made of separate pieces is that the joint, connection, or brazing is, of necessity, made of a different material than the gripping arms of the tweezers. Because tweezers many times are exposed to moisture, it has been found that corrosion and rust resistance is diminished because of the presence of different types of metals in contact with one another.

Rust or corrosion, especially at the joint for the tweezers, could impair its operation or its continued use. Therefore, one method to eliminate this problem would be to construct the tweezers entirely of one material.

It is also noted that a significant problem with regard to manufacturing costs exists in that conventional two or more piece tweezers handles require more manufacturing steps, which means more cost.

It is therefore a principal object of the present invention to provide tweezers which improve over or solve the problems in the art.

A further object of the present invention is to provide tweezers and tweezers handles which are made from a single piece of material.

Another object of the present invention is to provide tweezers which are made from a single type of material.

Another object of the present invention is to provide tweezers which are very resistive to corrosion.

Another object of the present invention is to provide tweezers which can be manufactured to high tolerances, and precise specifications.

Another object of the present invention is to provide tweezers which can be manufactured economically.

A further object of the present invention is to provide tweezers which are accurate, precise, and durable.

These and other objects, features, and advantages of the present invention will become apparent with reference to the accompanying specification and drawings.

SUMMARY OF THE INVENTION

The present invention utilizes tweezers and tweezers handles made of a single piece of material. By manufacturing the tweezers or tweezers handles out of one piece of metal material, corrosion is resisted much better than tweezers which contain different types of metal material.

One preferred embodiment of the present invention has a unitary body, including two parallel spaced apart gripping arms which extend from a heel end portion. No bending or forming of the tweezers is required after cutting the tweezers from the single piece of material, other than possibly bending the arms slightly outward so that they are biased to an open position. A second preferred embodiment has a unitary, single-piece tweezers handle made of two spaced apart handle members extending from a heel end portion. Replaceable gripping tips made from the same material as the handle comprise the working end of the tweezers. The terms "single-piece tweezers" is to be understood to cover both types of embodiments.

A preferred method for producing the single piece tweezers or tweezers handles involves the use of electrical discharge machine (EDM) process. In particular, a traveling wire electrical discharge machine can be used to cut the tweezers out of metal material with extremely high precision. EDM also requires little post-cutting finishing. This allows the economical production of very precise or small instruments, such as those used in surgery or microsurgery.

BRIEF DESCRIPTION OF THE DRAWINGS

FIG. 1 is a perspective view of one embodiment of a single piece tweezers according to the present invention.

FIG. 2 is a perspective view of a second embodiment of a single-piece tweezers handle with accompanying replaceable tips according to the present invention.

FIG. 3 is an enlarged side view of the embodiment of FIG. 1.

FIG. 4 is an enlarged top view of the embodiment of FIG. 1.

FIG. 5 is an enlarged side view of the embodiment of FIG. 2.

FIG. 6 is an enlarged top view of the embodiment of FIG. 2.

FIG. 7 is a further enlarged fragmented perspective view of tweezer tip ends similar to those of the embodiments in FIGS. 1 and 2.

DETAILED DESCRIPTION OF THE PREFERRED EMBODIMENT

With reference to the drawings, and particularly FIG. 1, there is shown a single-piece tweezers 10 according to the present invention. It is again pointed out that "single-piece tweezers" refers to both embodiments such as is shown in FIGS. 1, 3 and 4 as well as that shown in FIGS. 2, 5 and 6. The entire tweezers can be literally made from a single-piece (FIGS. 1, 3 and 4) or just the handle portion (FIGS. 2, 5 and 6). Tweezers 10 includes parallel spaced-apart arms 12 and 14 which extend from a heel portion 16. The entire tweezers 10 is made from a single piece of material. In the preferred embodiment of FIG. 1, the material can be stainless steel. Arms 12 and 14 are slightly sprung so that they are biased in a normally open position ready for use. Tip sections 18 and 20 are part of the unitary body of tweezers 10 and are of corresponding shape to one another.

Protrusions 22 are integral with the outer body of tweezers 10 and enhance gripability of handles 12 and 14. Stop members 24 and 26 extend generally perpendicular from the innerfacing surfaces of arms 12 and 14, and are aligned to come into abutment when handles 12 and 14 are converged towards one another. The height of stop members 24 and 26 can be accurately manufactured so that they come into abutment and stop further convergence of arms 12 and 14 so that the very ends of tip sections 18 and 20 also come into abutment, but that no bending or deforming of the tip sections 18 and 20 takes place which might cause sections 18 and 20 to gap. As can be seen in FIG. 3, tip sections 18 and 20 are manufactured so that a gap 28 exists between them even though outer tip ends 30 and 32 are in abutment. Stop members 24 and 26 stop any movement which might deform tip sections 18 and 20 and experience the majority of any force trying to further converge arms 12 and 14 together.

FIGS. 3 and 4 also better show the specific shape of the embodiment of FIG. 1 with its precise features.

FIG. 2 depicts a second embodiment of tweezers 34 which are essentially the same as tweezers 10 except that arms 36 and 38 are shorter. Additionally, tip sections 40 and 42 are removable from arms 36 and 38 by virtue of key members 44 and 46 which matably fit within slot members 48 and 50. Tip sections 40 and 42 are therefore interchangeable with the unitary, single-piece body of tweezers 34 so that if they are damaged or need service, this can easily be accomplished. In the preferred embodiment, key members 34 and 46 are secured by interference fit into slots 40 and 50. That is, the diameter of key members 44 and 46 is slightly larger than slots 48 and 50. It is to be understood, however, that tip sections 40 and 42 will still be made out of the same type of metal as arms 36 and 38 so that corrosion will continue to be resisted.

FIGS. 5 and 6 show with more detail the specific features of tweezers 34.

FIG. 7 shows, in further enlarged detail, one embodiment of the precise outer tip ends 30 and 32 of tweezers 10. Outer tip ends 30 and 32 are basically L-shaped in configuration but have minute features including tooth 52 extending from outer tip section 30 and teeth 54, 56, and V-slot 58 on outer tip end 32. Also, there are raised edges 60 and 62 inward along outer tip ends 30 and 32.

The preferred method for creating single-piece tweezers such as described above is by use of traveling wire electrical discharge (EDM) machines which allow the precise, accurate, and economical cutting of instruments from any electrical conducting material such as stainless steel, for example. Traveling wire electrical discharge machine process is known in the art and machinery and controlling mechanisms to perform these functions are available from various companies including Charmilles Corporation of America, 58 Enter Lane, Hauppauge, N.Y. 11787.

Producing items such single-piece tweezers provides the advantages above discussed and also reduces the cost of production. Electrical discharge machines (EDM machines) present a desirable method for making tweezers according to the present invention because of the ability for extreme precision for many types of cuts. Precision can be made within 1/10,000ths of an inch to allow the intricate detail such as shown in FIG. 7. All that is required to finish implements such as the tweezers is some polishing, which is vastly less than is required to finish items made by other conventional methods.

It is to be noted that arms 12 and 14 of single-piece tweezers 10 of FIGS. 1, 3 and 4 can be manufactured so that they taper from being thin at or near heel 16 and then become increasingly thicker towards tip sections 18 an 20. This is particularly depicted in FIG. 3. Such tapering is beneficial as it increases torsional stability of tweezers 10, which is critical for long-armed tweezers. This can be compared to the alternative embodiment of tweezers 34 in FIG. 5. Additionally such precise tapering is easily accomplished by the EDM process and machines.

It is to be understood, however, that other methods could be used to produce single-piece tweezers according to the present invention.

It is to be understood that the included preferred embodiment is given by way of example only, and not by way of limitation to the invention, which is solely described in the claims herein. Variations obvious to one skilled in the art will be included within the invention defined by the claims.

What is claimed is:

1. A single-piece tweezers body means comprising:
   a unitary body member including a heel end portion and first and second generally parallel, elongated, spaced apart arm portions, each having first and second corresponding ends, and facing surfaces between the ends, said arm portions formed integrally with the heel end portion at said first ends, said unitary body member being comprised of one piece of high tensile strength, rigid yet resilient material;
   said arm portions being comprised of rear sections generally thin, elongate, and flat with respect to the facing surfaces of the arm portions having a thin cross-section and extending from the heel end portion to handle sections,
   the handle sections also being generally elongate and flat but of thicker cross-section than the rear sections, the handle sections extending to working end sections which are elongate and thin in width and length and narrower in cross-section than the handle sections;
   said arms diverging slightly away from one another at or around the junction of the rear and handle sections, and converging slightly at or around the junction of the handle and working end sections; and
   protrusions extending perpendicularly from the inner-facing surfaces of the handle sections of the arm portions which come into abutment upon closing the tweezers body means to serve as stops to prevent gapping of the working end sections of the arm portions of the tweezers body means.

2. The device of claim 1 wherein said unitary body is formed by cutting said body from a single piece of material by electrical discharge machine process.

3. The device of claim 2 wherein said electrical discharge machine process utilizes a traveling wire for cutting the material.

4. The device of claim 1 wherein said arms are cut so as to have a gap between at least a portion of the arms.

5. The device of claim 1 wherein said gripping arms are forceably bent apart to produce a spring bias so that the gripping arms are normally in an open, spaced apart position.

6. The device of claim 1 wherein said tweezers comprise surgical tweezers.

7. The device of claim 1 wherein said arms comprise handle portions adjacent to and extending from the heel end portion, and gripping portions extending from the handle portions.

8. The device of claim 1 wherein said arms comprise handle portions having first ends adjacent to and extending from the heel end portion, and having second ends which are attachable to replaceable gripping tips.

9. The device of claim 8 wherein the gripping tips are made from the same material as the unitary body member.

10. The device of claim 1 wherein the working end sections are generally aligned with the longitudinal axes of the first and second arm portions.

11. The device of claim 7 wherein the working end sections of the arm portions extend so that the gripping sections are offset from the general longitudinal axis of the first and second arm portions.

12. The device of claim 8 wherein the replaceable gripping sections are made of material having at least closely similar properties as the material of the arm portions, and which have key means which are frictionally fittable into slot means in the working end sections of the arm portions.

13. The device of claim 7 wherein said gripping sections include inwardly extending raised members forming gripping areas.

14. A method for producing one-piece tweezers body means comprising the steps of:

cutting a unitary body member from a single piece of high tensile strength, rigid yet resilient material, said body member including first and second generally parallel, elongated spaced apart arm portions, each having first and second ends, said arm portions formed integrally with a heel end portion, the second ends of the arm portions opposite the heel end portion comprising working end sections of the body member;

said arm portions being cut so as to have rear sections generally thin elongate and flat with respect to innerfacing surfaces of the arm portions and having a thin cross-section and extending from the heel end portion to handle sections, the handle sections also being elongated and flat but of thicker cross-section, the handle sections extending to the working end sections which are elongated and thin in width and length and narrower in cross-section than the handle sections;

bending said arm portions so that said first and second arm portions diverge slightly away from one another at or around the junction of the rear and handle sections;

cutting said arm portions so that they converge slightly at or around the juction of the handle and working end sections.

15. The method of claim 14 wherein the material is cut by electrical discharge machine process.

16. The method of claim 15 wherein the electrical discharge machine process uses a traveling wire for cutting the material.

17. The method of claim 14 wherein said tweezers comprise surgical tweezers.

18. The method of claim 14 wherein said working end portions are cut so as to extend to an offset position from the longitudinal axis of the gripping arms.

19. The method of claim 14 wherein the working end portions and tweezer tips are made from the same material as the remaining portions of the gripping arms, and are separable from those remaining portions by having key members which are frictionally fittable into slot members in the handle portions of the gripping arms.

20. The method of claim 14 wherein the working end sections include a gripping section.

21. The method of claim 14 wherein the working end sections are adapted to receive a removable gripping section.

* * * * *